US011170888B2

(12) United States Patent
Angelides

(10) Patent No.: US 11,170,888 B2
(45) Date of Patent: Nov. 9, 2021

(54) CAPTURING CROWD WISDOM IN INDIVIDUALIZED TREATMENT PLANS

(71) Applicant: Vivante Health, Inc., Houston, TX (US)

(72) Inventor: Kimon Angelides, Houston, TX (US)

(73) Assignee: VIVANTE HEALTH, INC., Houston, TX (US)

( * ) Notice: Subject to any disclaimer, the term of this patent is extended or adjusted under 35 U.S.C. 154(b) by 0 days.

(21) Appl. No.: 16/735,427

(22) Filed: Jan. 6, 2020

(65) Prior Publication Data

US 2020/0168315 A1 May 28, 2020

(51) Int. Cl.

| | |
|---|---|
| ***C12M 1/00*** | (2006.01) |
| ***G01N 1/22*** | (2006.01) |
| ***G16H 20/60*** | (2018.01) |
| ***C12Q 1/689*** | (2018.01) |
| ***C12Q 1/6883*** | (2018.01) |
| ***G16H 50/70*** | (2018.01) |
| ***G16H 10/40*** | (2018.01) |
| ***G16H 20/90*** | (2018.01) |

(Continued)

(52) U.S. Cl.

CPC ............. *G16H 20/60* (2018.01); *C12Q 1/689* (2013.01); *C12Q 1/6883* (2013.01); *G06Q 50/01* (2013.01); *G16H 10/40* (2018.01); *G16H 20/90* (2018.01); *G16H 50/50* (2018.01); *G16H 50/70* (2018.01); *C12Q 2600/106* (2013.01); *C12Q 2600/156* (2013.01); *C12Q 2600/158* (2013.01); *G01N 1/2226* (2013.01); *G01N 1/2294* (2013.01); *G01N 2001/2244* (2013.01); *G01N 2001/2297* (2013.01)

(58) Field of Classification Search

None

See application file for complete search history.

(56) References Cited

U.S. PATENT DOCUMENTS 5,359,038 A * 10/1994 Padron ................ C07K 16/065 530/387.1
8,933,292 B2 * 1/2015 Abraham ................ A61F 13/42 604/361
9,562,915 B2 * 2/2017 Burgi .................... G01N 33/98

(Continued)

FOREIGN PATENT DOCUMENTS

WO WO 2016/063148 A1 * 4/2016 ........... G01N 33/483

OTHER PUBLICATIONS

Binder, Henry J. "Causes of chronic diarrhea." New England Journal of Medicine 355.3 (2006): 236.*

(Continued)

*Primary Examiner* — Anna Skibinsky
(74) *Attorney, Agent, or Firm* — Eric P Mirabel, LLM

(57) ABSTRACT

Embodiments of the invention include systems and methods for capturing crowd wisdom to be tested for individualized treatment plans. These systems and methods include data mining crowd sourced health related information and unstructured medical narratives and storytelling to identify treatment plans and general techniques that individuals with chronic diseases/symptoms, including but not limited to IBD and other immune invisible neglected and stigmatized diseases, use to improve their general health and wellbeing. A system for testing the treatments effectiveness in a population and then in an individual is also disclosed.

9 Claims, 10 Drawing Sheets

(51) Int. Cl.
*G16H 50/50* (2018.01)
*G06Q 50/00* (2012.01)

(56) References Cited

U.S. PATENT DOCUMENTS

| | | | | |
|---|---|---|---|---|
| 10,587,545 | B1 | 3/2020 | Bitoun et al. | |
| 2004/0006257 | A1* | 1/2004 | Burch | A61B 5/00 600/300 |
| 2011/0192213 | A1* | 8/2011 | Zimmerman | A01K 5/0225 73/23.3 |
| 2014/0148357 | A1* | 5/2014 | Aune | C12Q 1/6883 506/9 |
| 2014/0343451 | A1* | 11/2014 | Pannell | A61B 1/31 600/562 |
| 2015/0313534 | A1 | 11/2015 | Angelides | |
| 2015/0317913 | A1 | 11/2015 | Angelides | |
| 2016/0033476 | A1* | 2/2016 | Blake | G01N 33/497 73/23.3 |
| 2016/0097761 | A1* | 4/2016 | Sano | G01N 33/497 73/23.3 |
| 2016/0195525 | A1* | 7/2016 | Evoy | C12Q 1/689 435/6.11 |
| 2016/0303173 | A1* | 10/2016 | Tsai | A61P 1/00 |
| 2016/0361678 | A1* | 12/2016 | Blackley | G01N 33/0011 |
| 2017/0076630 | A1 | 3/2017 | Angelides | |
| 2018/0119973 | A1* | 5/2018 | Rothman | G05B 15/02 |
| 2018/0271404 | A1* | 9/2018 | Gupta | A61B 5/097 |
| 2019/0249221 | A1* | 8/2019 | Rodriguez-Palacios | C12Q 1/28 |
| 2020/0015707 | A1* | 1/2020 | Ratto | A61B 5/082 |

OTHER PUBLICATIONS

Rezaie, Ali, et al. "Hydrogen and methane-based breath testing in gastrointestinal disorders: the North American Consensus." The American journal of gastroenterology 112.5 (2017): 775.*

Bosch, Sofie, et al. "Fecal volatile organic compounds for early detection of colorectal cancer: where are we now?." Journal of cancer research and clinical oncology 145.1 (2019): 223-234.*

Wu, Huadong, and Mel Siegel. "Odor-based incontinence sensor." Proceedings of the 17th IEEE Instrumentation and Measurement Technology Conference [Cat. No. 00CH37066]. vol. 1. IEEE, 2000.*

Gao, F., et al. "DH2. 3-Virtual Electronic Nose for Simultaneous Detection of Hydrogen and Methane in Breath on the Diagnosis of Gastrointestinal Diseases." Proceedings IMCS 2018 (2018): 149-150.*

De Meij, Tim GJ, et al. "Early detection of necrotizing enterocolitis by fecal volatile organic compounds analysis." The Journal of pediatrics 167.3 (2015): 562-567.*

Patel, Nisha, et al. "Metabolomic analysis of breath volatile organic compounds reveals unique breathprints in children with inflammatory bowel disease: a pilot study." Alimentary pharmacology & therapeutics 40.5 (2014): 498-507.*

Kurada, S., et al. "breath analysis in inflammatory bowel diseases." Alimentary pharmacology & therapeutics 41.4 (2015): 329-341.*

* cited by examiner

For Individual X:

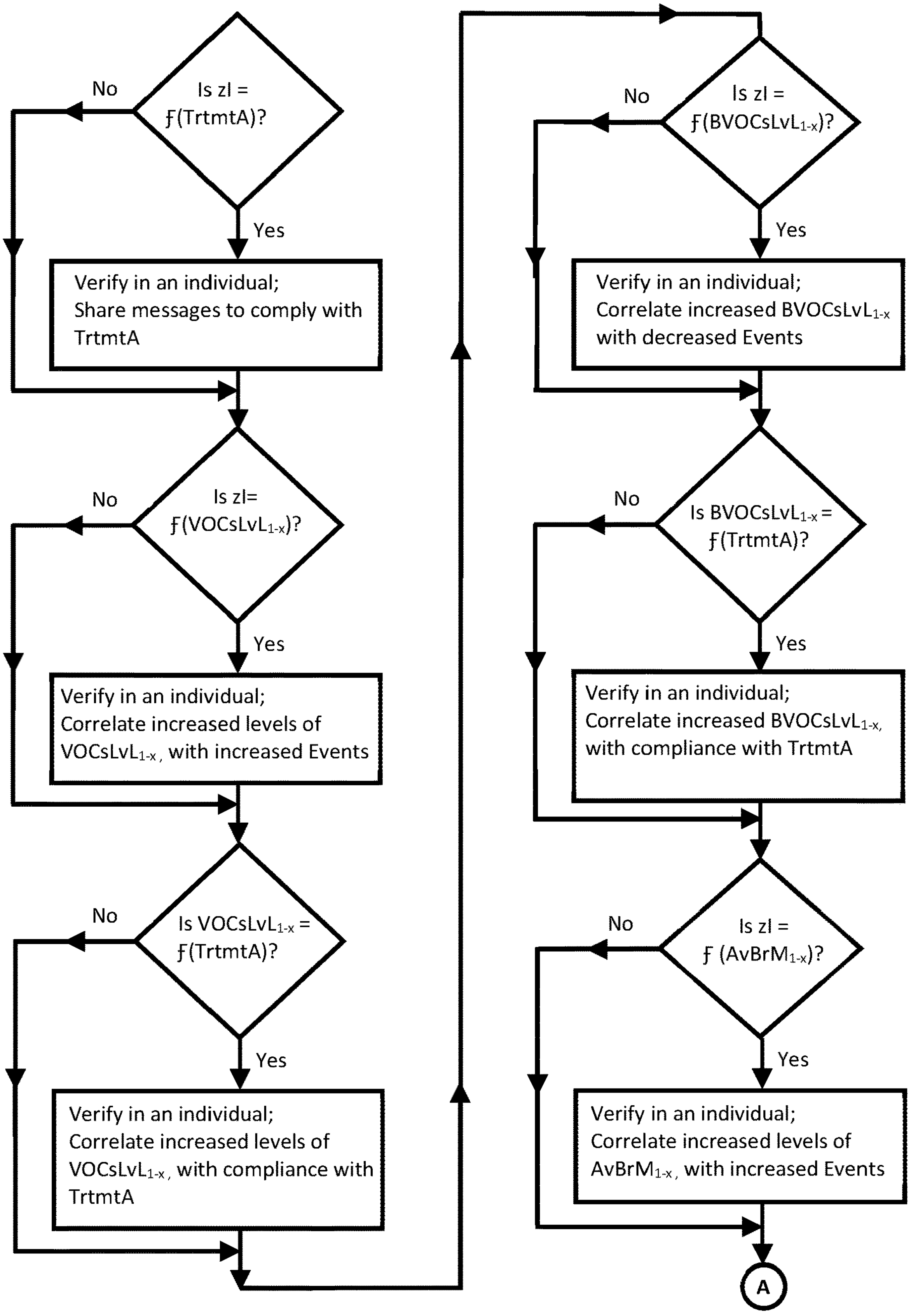

FIG. 6A

Left column (top to bottom):

- Decision: Is $zl = f(TrtmtA)$?
  - No → loop back
  - Yes → Verify in an individual; Share messages to comply with TrtmtA

- Decision: Is $zl = f(VOCsLvL_{1-x})$?
  - No → loop back
  - Yes → Verify in an individual; Correlate increased levels of $VOCsLvL_{1-x}$ with increased Events

- Decision: Is $VOCsLvL_{1-x} = f(TrtmtA)$?
  - No → loop back
  - Yes → Verify in an individual; Correlate increased levels of $VOCsLvL_{1-x}$ with compliance with TrtmtA

Right column (top to bottom):

- Decision: Is $zl = f(BVOCsLvL_{1-x})$?
  - No → loop back
  - Yes → Verify in an individual; Correlate increased $BVOCsLvL_{1-x}$ with decreased Events

- Decision: Is $BVOCsLvL_{1-x} = f(TrtmtA)$?
  - No → loop back
  - Yes → Verify in an individual; Correlate increased $BVOCsLvL_{1-x}$ with compliance with TrtmtA

- Decision: Is $zl = f(AvBrM_{1-x})$?
  - No → loop back
  - Yes → Verify in an individual; Correlate increased levels of $AvBrM_{1-x}$ with increased Events

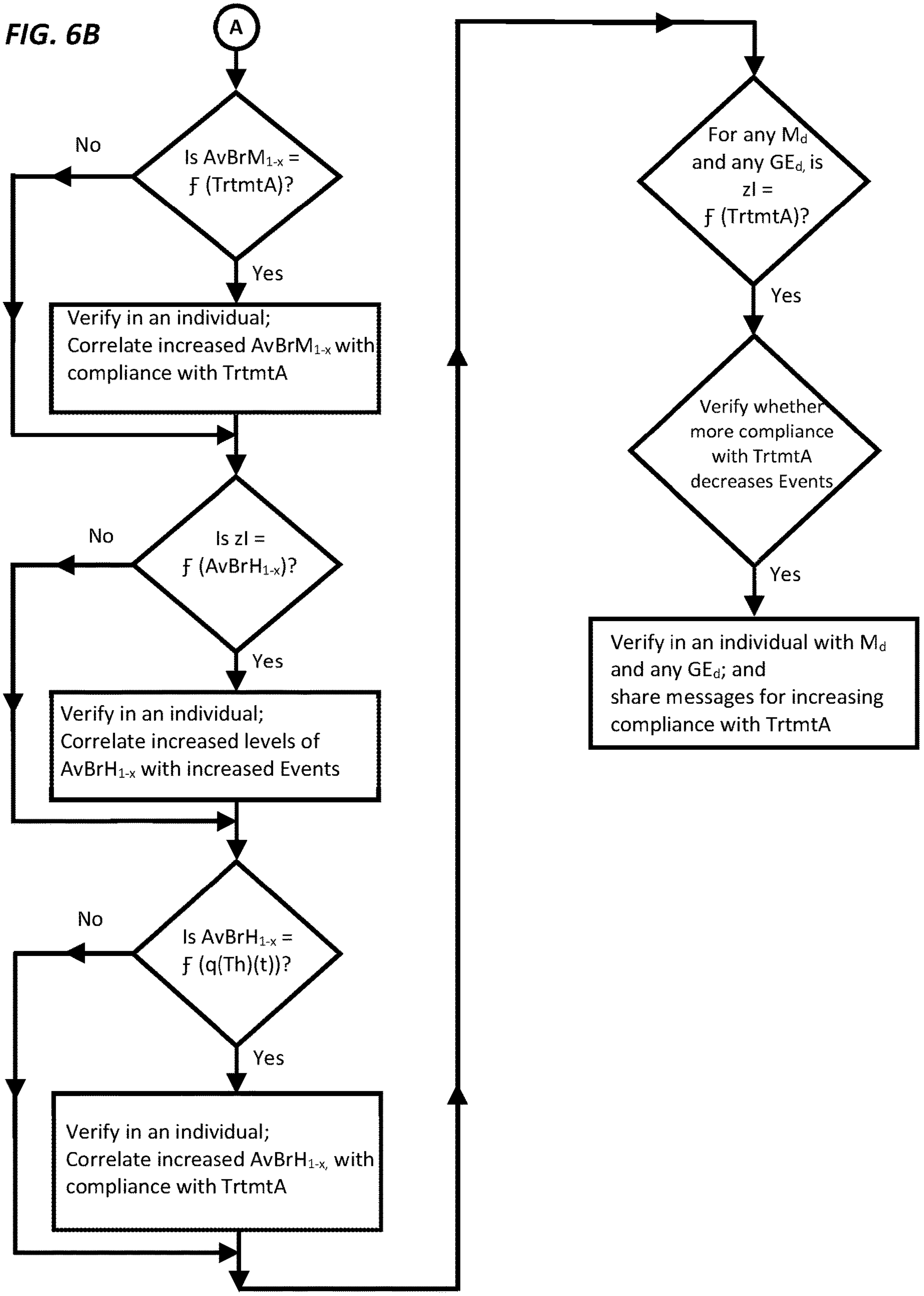

```
         (A)
          ↓
    ┌───────────┐
No  │ Is AvBrM₁₋ₓ = │
◄───┤ ƒ (TrtmtA)?   │
    └───────────┘
          │ Yes
          ▼
    ┌────────────────────────┐
    │ Verify in an individual; │
    │ Correlate increased AvBrM₁₋ₓ with │
    │ compliance with TrtmtA │
    └────────────────────────┘
          │
          ▼
    ┌───────────┐
No  │ Is zl =   │
◄───┤ ƒ (AvBrH₁₋ₓ)? │
    └───────────┘
          │ Yes
          ▼
    ┌────────────────────────┐
    │ Verify in an individual; │
    │ Correlate increased levels of │
    │ AvBrH₁₋ₓ with increased Events │
    └────────────────────────┘
          │
          ▼
    ┌───────────┐
No  │ Is AvBrH₁₋ₓ = │
◄───┤ ƒ (q(Th)(t))? │
    └───────────┘
          │ Yes
          ▼
    ┌────────────────────────┐
    │ Verify in an individual; │
    │ Correlate increased AvBrH₁₋ₓ with │
    │ compliance with TrtmtA │
    └────────────────────────┘
```

Is $\mathrm{AvBrM}_{1-x}$ = ƒ(TrtmtA)?

Verify in an individual; Correlate increased $\mathrm{AvBrM}_{1-x}$ with compliance with TrtmtA Is $zl$ = ƒ($\mathrm{AvBrH}_{1-x}$)?

Verify in an individual; Correlate increased levels of $\mathrm{AvBrH}_{1-x}$ with increased Events Is $\mathrm{AvBrH}_{1-x}$ = ƒ(q(Th)(t))?

Verify in an individual; Correlate increased $\mathrm{AvBrH}_{1-x}$ with compliance with TrtmtA For any $M_d$ and any $GE_d$, is $zl$ = ƒ(TrtmtA)?

Verify whether more compliance with TrtmtA decreases Events

Verify in an individual with $M_d$ and any $GE_d$; and share messages for increasing compliance with TrtmtA For Test Subjects:

For Individual X:

CAPTURING CROWD WISDOM IN INDIVIDUALIZED TREATMENT PLANS

BACKGROUND

Anyone facing a chronic disease or consistent discomfort must typically rely on health care professionals and other sources, like the internet, including blogs, to assess various treatment alternatives. The public information is typically derived from medical records, publications, and/or from structured information derived from questionnaires and structured interviews by health care professionals. Such data and information from questionnaires and structured interviews is limited and often does not capture the more nuanced responses of the participating individuals.

Although people share the same disease or the same chronic symptomology, their ability to navigate through the symptoms often will include personal adjustments to their daily routines. Many people facing chronic diseases and symptoms will try alternative approaches that they are unwilling to share with their physicians so that they do not appear in their medical records or in any of the structured data used to map treatment plans and their success.

One such group of chronic illness, affecting as much as 74% of the American population, are chronic digestive diseases such as celiac disease, Crohns disease, irritable bowel syndrome, or ulcerative colitis (collectively, "inflammatory bowel disease" or "IBD") affect at least 70 million people. Such alternative treatments for IBD abound, including herbal remedies, supplements, acupuncture or acupressure, relaxation techniques, or exercise regimes such as yoga or stretching. Patients may also unknowingly and unwittingly expose themselves to effective treatments, and then repeat certain activities or consume certain products, to continue to reap the benefits; while not understanding the portion of the activity or the active ingredients in products which is associated with symptom relief. The effectiveness of all such alternative therapies is unknown, and the IBD patient must try a wide array of such therapies and then try to decide which worked and which did not. Making such determinations is difficult, due to the lack of objectivity in personal observation, and the lack of control (i.e., failure to exclude other possibly relevant factors) in such self-directed analysis.

Evaluating effective alternative IBD treatments is more difficult than making wise dietary choices; even though certain foods are known to exacerbate the problem. Symptom relief has been achieved with a low-FODMAP diet (low in fermentable sugars) in a large majority of functional gastrointestinal disorders patients with fructose or lactose intolerance. Wilder-Smith et al., "Predictors of response to a low-FODMAP diet in patients with functional gastrointestinal disorders and lactose or fructose intolerance." Aliment Pharmacol Ther 2017 April; 45(8):1094-1106. Nevertheless, it is difficult for a patient to determine which foods may not be low-FODMAP. It is even more difficult to be sure a treatment is in fact effective.

It would be markedly advantageous if the effectiveness of treatments could be determined based on a set of indicators which could be monitored to indicate the relative state of the subject's health.

SUMMARY

As a first step in evaluating alternative therapies, one would review the patients in a database and determine which treatments generated symptom relief, or which generated positive changes in the microbiome. In humans, the gut contains the largest numbers of bacteria and the greatest number of species of bacteria of any area of the human body. An individual's general health and well being is dependent on the proper balance of the bacterial populations in the gut. Imbalances in the intestinal bacterial flora are associated with a number of digestive and immunological disorders. The presence or overabundance of certain types of bacteria have been reported to contribute to obesity, inflammatory bowel diseases, irritable bowel syndrome and other inflammatory or autoimmune conditions. The microbiome composition can thus be an objective indicator of effectiveness of alternative therapies.

Symptom relief can be measured by querying the patient, or by monitoring a number of parameters, including factors like clinical and psychosocial conditions; adherence to recommended medication and nutrition for IBD; biometrics at the point of care; usage & engagement in activities; absenteeism; presenteeism; medical and pharmacy claims history; and medical records. In addition to the microbiome composition, other objective indicators can indicate effectiveness of alternative therapies, including gut methane and hydrogen production, as well as other volatile compounds.

Regarding methane and hydrogen production, animal model experiments have shown that methane, a gaseous by-product of intestinal bacteria, slows small intestinal transit and appears to do so by augmenting small bowel contractile activity. Pimentel M, et al., "Methane, a gas produced by enteric bacteria, slows intestinal transit and augments small intestinal contractile activity." Am J Physiol Gastrointest Liver Physiol 2006; 290: G1089-95. In the lactulose breath test (where the patient is challenged with lactulose and then methane production is measured), methane in the breath of IBS patients has been associated with severity of constipation. Chatterjee S, "The degree of breath methane production in IBS correlates with the severity of constipation." Am J Gastroenterol 2007; 102: 837-41. Elevated hydrogen production, as measured in the breath, is also widely believed to be associated with symptoms in inflammatory bowel disease.

The levels of certain volatile organic metabolites in the feces of patients with IBD and healthy controls are indicators of IBD. Ahmed, I. et al. "An Investigation of Fecal Volatile Organic Metabolites in Irritable Bowel Syndrome," PLoS One. 2013; 8(3): e58204. These researchers arrived at a list of 28 such volatile metabolites associated ("VOCs") with IBD and not healthy controls, and a list of 11 such volatile metabolites associated with healthy controls and not with IBS.

TABLE A

| S. No. | Compounds |
|---|---|
| 1 | Butanoic acid, ethyl ester |
| 2 | Propanoic acid, methyl ester |
| 3 | 1-Methyl-2-(1-methylethyl)-benzene |
| 4 | Butanoic acid, butyl ester |
| 5 | Butanoic acid, propyl ester |
| 6 | Hexanoic acid, methyl ester |
| 7 | Propanoic acid, propyl ester |
| 8 | Acetic acid, butyl ester |
| 9 | Butanoic acid, 3-methyl-, butyl ester |
| 10 | Propanoic acid, butyl ester |
| 11 | Cyclohexanecarboxylic acid, ethyl ester |
| 12 | Butanoic acid, 2-methyl-, propyl ester |
| 13 | Ethanoic acid, ethyl ester |
| 14 | Pentanoic acid, 4-methyl |
| 15 | Acetic acid, pentyl ester |

TABLE A-continued

| S. No. | Compounds |
|---|---|
| 16 | Pentanoic acid, butyl ester |
| 17 | Butanoic acid, 3-methyl-, propyl ester |
| 18 | Cyclohexanecarboxylic acid, propyl ester |
| 19 | 6-Methyl-5-hepten-2-one |
| 20 | Propanoic acid, 3-methyl-butyl ester |
| 21 | Ethanoic acid, 3-methyl-I-butyl ester |
| 22 | Cyclohexanecarboxylic acid, butyl ester |
| 23 | Benzoic acid, 2-hydroxy-, methyl ester |
| 24 | Pentanoic acid, 4-methyl-, pentyl ester |
| 25 | Butanoic acid, 3-methyl-, methyl ester |
| 26 | Thiopivalic acid |
| 27 | 5-Methyl -2-(1-methylethyl)-cyclohexanone |
| 28 | 4-Methyl-1-Indole |

TABLE B

| | |
|---|---|
| 1 | 2-Heptanone |
| 2 | 2-Methylpropanal |
| 3 | 3-Methylbutanoic acid |
| 4 | Undecane |
| 5 | 3-Methylbutanal |
| 6 | 2-Methylpropanoic acid |
| 7 | 2-Methyl-1-propanol |
| 8 | 1R-a-Pinene |
| 9 | 2-Penhifizran |
| 10 | Methoxy-phenyl-oxime |
| 11 | 2-Methylfuran |

These compounds could be detected in a fecal sample to indicate the presence of IBD, or the likelihood that it is in remission or symptoms have alleviated (where the compounds in Table B predominate). More importantly, they could be used to determine the effectiveness of alternative therapies for amelioration of IBD, by determining which therapies cause increases or decreases in these volatile metabolites, first in a group of test subjects using AI/software agents, then in each individual who would be a participant, who could be monitored for these metabolites while using the alternative therapy and controlling for other factors, like diet, which could affect the results. With that information for the individual a software agent would determine treatments to ameliorate IBD for the individual.

As a first step in evaluating an alternative therapy, one would find correlations, in patient feces, between certain genetic markers indicative of mutant subspecies of the bacteria in the gut, certain levels of gene expression, certain levels of volatile organic compounds (VOCs) and certain levels of methane and hydrogen in patient breath (or feces), certain levels of gut bacteria making up the microbiome; and negative symptomology ("Events"), as determined in a group of test subjects. After establishing those correlation, one can use them in finding therapies which prevent, reduce incidence of or otherwise reduce Events or alleviate symptoms by finding in test subjects correlations between practicing such therapies and levels (i) of VOCs in patient feces, and levels (ii) of methane and hydrogen in patient breath (or feces), and optionally, (iii) microbiome composition (including as determined from fecal genetic markers), or (iv) gene expression. The final step is to determine which levels of (i), (ii), (iii) and/or (iv) can serve as indicators of a therapy which reduces Events. Where a subject has levels of (i), (ii), (iii) and/or (iv) indicating that the alternative therapy is efficacious, but does not report a concomitant reduction in frequency of Events, this can indicate the therapy is not being properly followed. Where a subject has levels of (i), (ii), (iii) and/or (iv) indicating that the alternative therapy is not efficacious, and reports a reduction in frequency of Events, this can indicate the subject is being benefited from some other means than the therapy. Such subjects can be queried to try to find the source of their symptom relief, and it can be subject to the same analysis against levels of (i), (ii), (iii) and/or (iv) as above to verify or refute its effectiveness.

Embodiments of the invention further include systems and methods for capturing crowd wisdom to be tested for individualized treatment plans. These systems and methods include data mining crowd sourced health related information and unstructured medical narratives and storytelling from patients to identify treatment plans and general techniques that individuals with chronic diseases/symptoms, including IBD, use to improve their general health and wellbeing. The crowd wisdom is captured by an information management system that obtains input from affected individuals about their preferred treatments, and from published information sources.

A related embodiment of the invention captures crowd wisdom by monitoring of subjects' parameters; including, both objective parameters and the self-reported parameters, in those subjects who report periodic or episodic symptom relief but are unaware of the source of relief. During periods of symptom relief, as verified by one or more of the parameters, the subjects' food and drug consumption, activities, travel, home environment, and other variables can be monitored to determine if the relief can be tied to any such variables.

The system of the invention provides a system to find potential treatments from public literature and from subjects themselves; determine indicators of IBD; verify the correlation of those indicators to a disease or amelioration state in an individual; place the individual on an unapproved treatment regime; and then verify or refute the treatment regime's effectiveness both by its effect on symptoms as reported by the individual, and by whether the objective indicators follow the expected pattern and correlate with the reported symptoms. Messages are preferably sent to reinforce compliance with the treatment regime, if the indicators do not follow the expected pattern and correlate with the reported symptoms.

The systems of the invention can be used in a similar manner to verify or refute treatments for other chronic conditions, besides IBD; provided a set of indicators for the status of the condition can be determined. These systems allow filtering out of ineffective treatments or disproving of correlations which don't in fact exist; such as "vaccines cause autism." Such ineffective treatments or nonexistent correlations may be widely touted and disseminated on the web or by social media; and therefore, widely accepted. Finding effective treatments and extant correlations to disease states is a significant public health benefit.

BRIEF DESCRIPTION OF THE FIGURES

FIGS. 6A and 6B show the equations representative of some of the steps in FIG. 5A, 5B.

Figure 1:
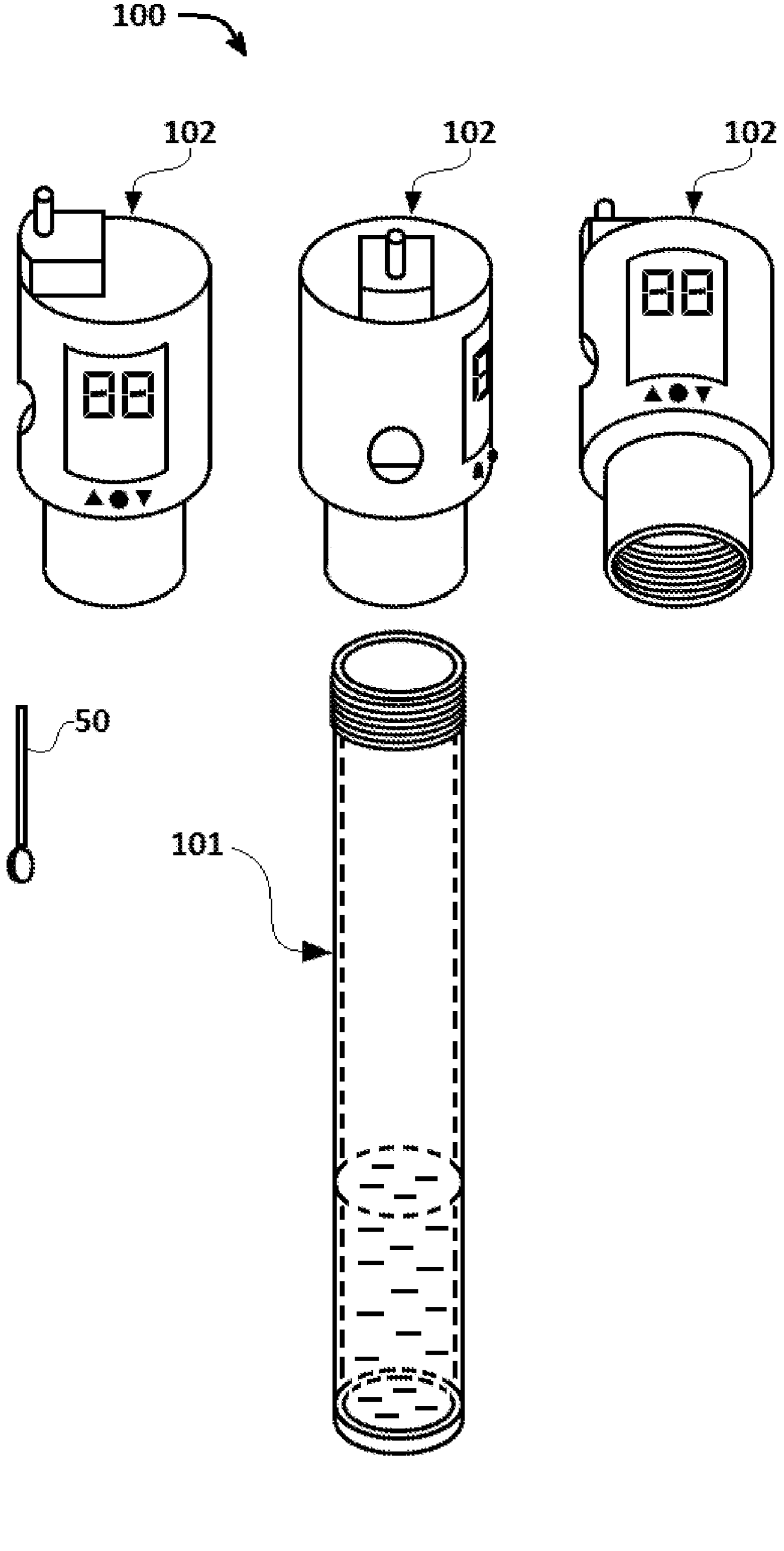
FIG. 1 is an exploded view of components of a fecal sample container and other components of a fecal sampling kit.
Figure 2:
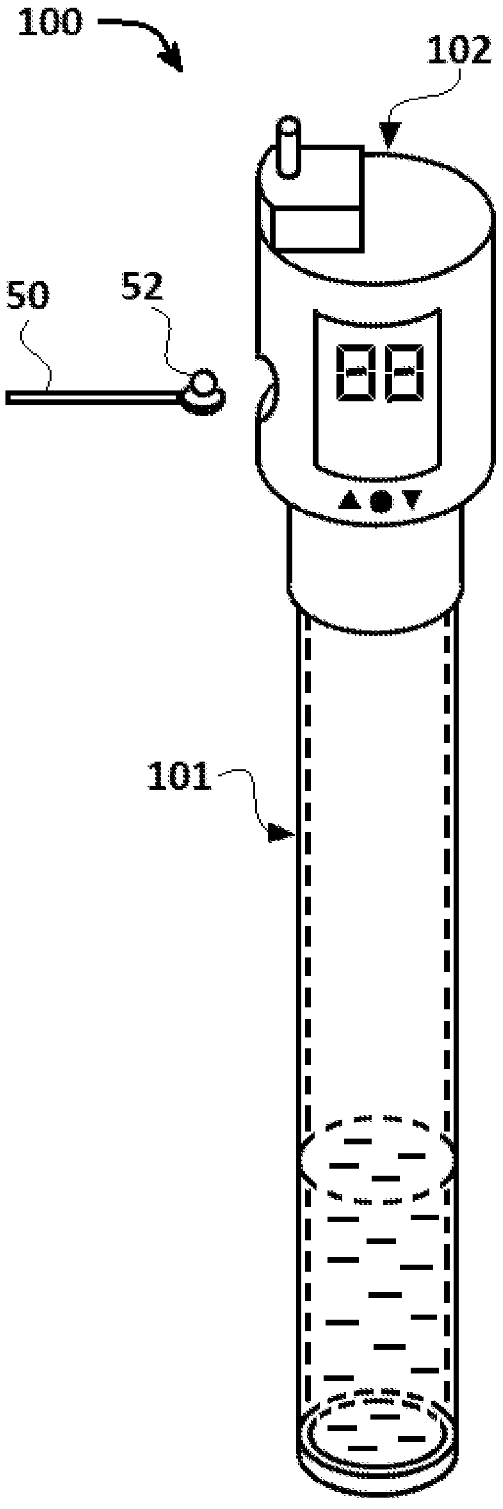
FIG. 2 is an assembled fecal sample container of the components shown in FIG. 1, with a fecal sample outside.
Figure 3C:
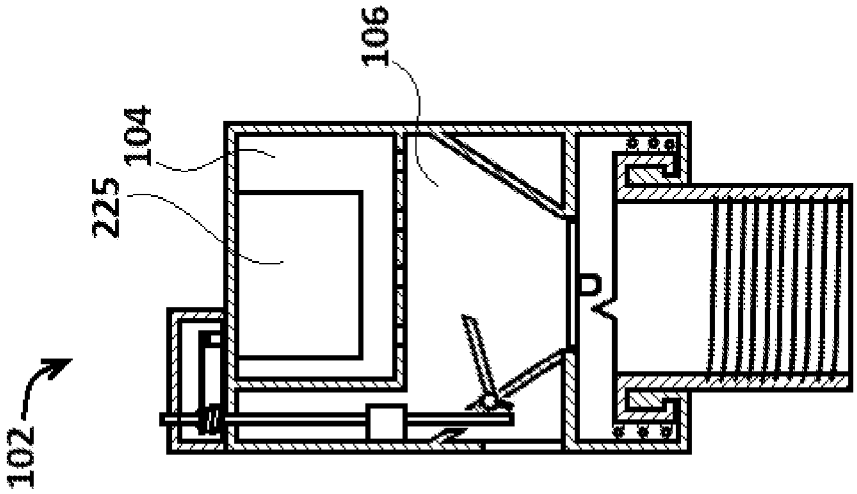
FIG. 3C is a sectional view of the upper part of the assembled fecal sample container taken along a vertical plane with the fecal port and port control in open position and the lower gate in chamber 106 closed.
Figure 3B:
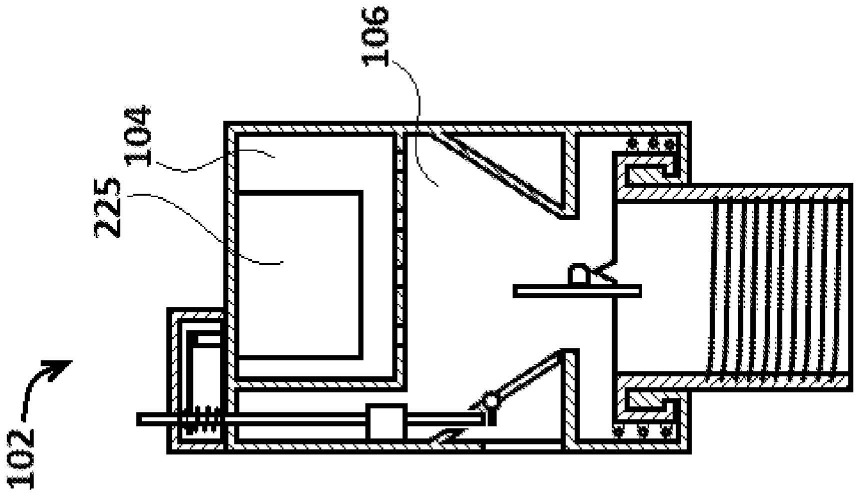
FIG. 3B is a sectional view of the upper part of the assembled fecal sample container taken along a vertical plane with the fecal port and port control in closed position and the lower gate in chamber 106 open.
Figure 3A:
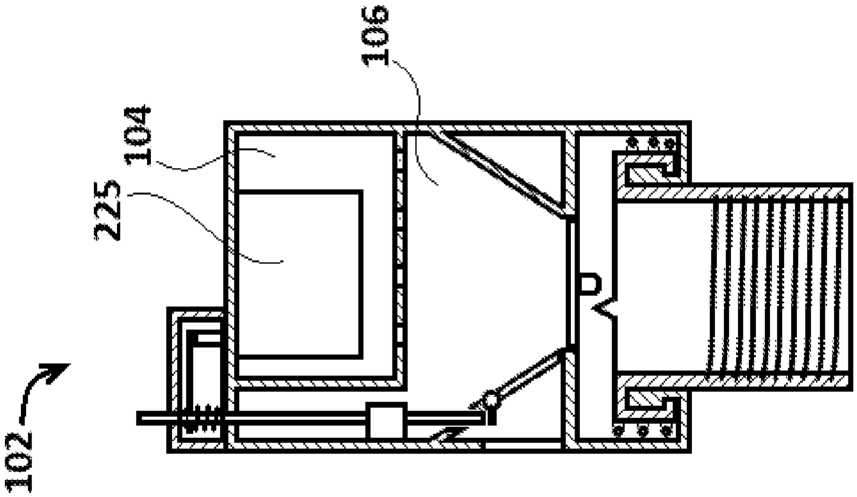
FIG. 3A is a sectional view of the upper part of the assembled fecal sample container taken along a vertical plane with the fecal port and port control in closed position and the lower gate in chamber 106 closed.
Figures 4A, 4B, 4C:
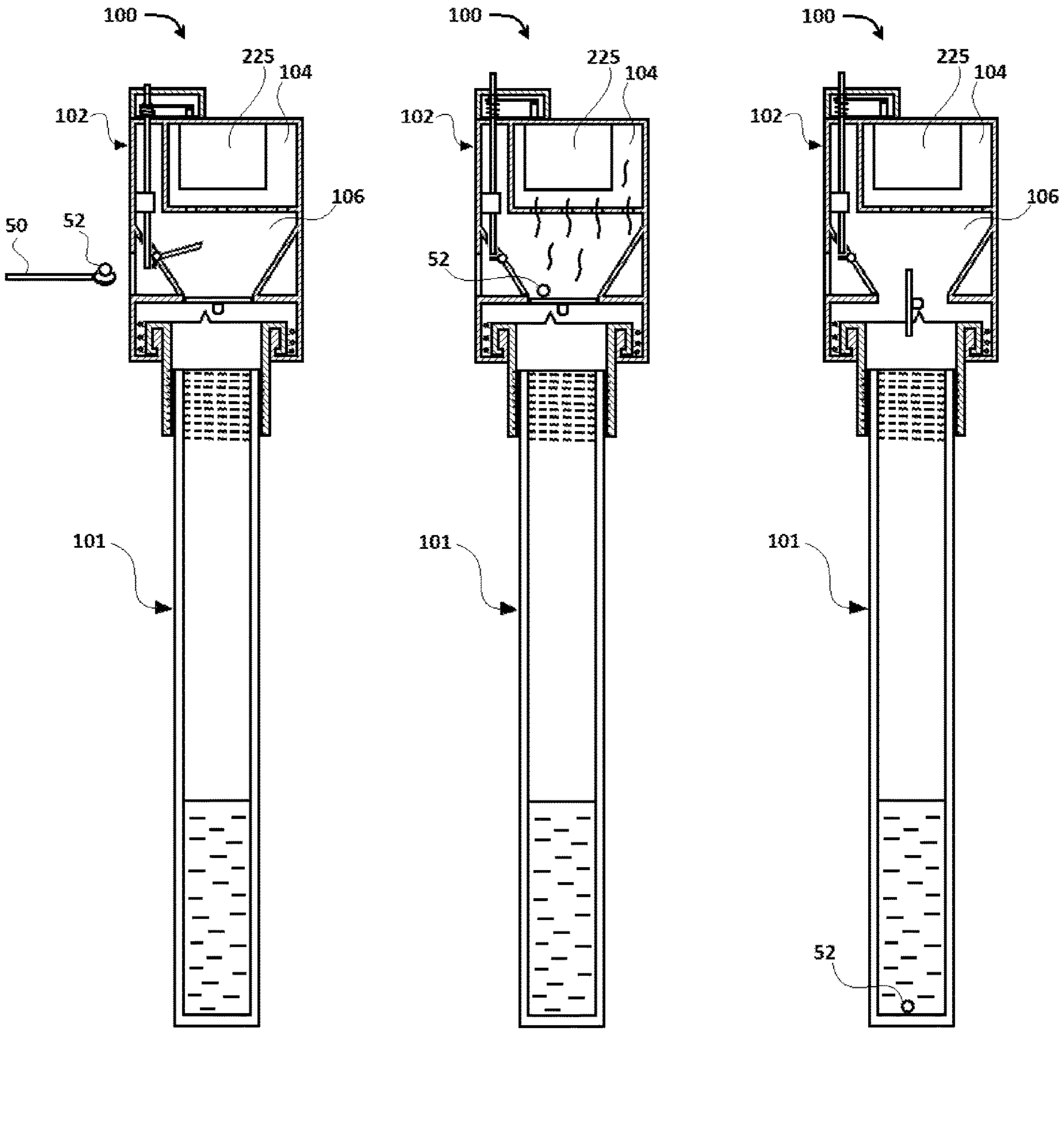
FIG. 4A is a sectional view of the fecal sample container taken along a vertical plane with the fecal port and port control in open position and the lower gate in chamber 106 closed.
FIG. 4B is a sectional view of the fecal sample container taken along a vertical plane with the fecal port and port control in closed position, a fecal sample in place in chamber 106, and the lower gate in chamber 106 closed.
FIG. 4C is a sectional view of the fecal sample container taken along a vertical plane with the fecal port and port control in closed position, and the lower gate in chamber 106 open, allowing the fecal sample to fall into the tube 101.

For a more complete understanding of the present invention, and the advantages thereof, reference is now made to the following description in conjunction with the accompanying drawings, outlined above.

DETAILED DESCRIPTION

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in Value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "comprising," when utilized, means "including, but not necessarily limited to"; it specifically indicates open-ended inclusion or membership in the so-described combination, group, series and the like.

It is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in any appropriately detailed structure.

It is proposed that significant insights into a person's health can be gained by analyzing crowd wisdom, based on aspects of home life, medical narratives, observations on effectiveness of treatments, and generally how diseased subjects operate on a daily basis. The types of insights gained by understanding a subject's social structure, daily routines and cultural background is important in understanding and personalizing that subject's experience and how they cope with chronic conditions or diseases. This type of unstructured data can be collated and analyzed to provide personalized treatment plans for other sufferers to adhere to provide positive changes in their quality of life. Thus, there is a need for processes that will capture a more inclusive set of data and related information from unstructured sources.

This invention is related to systems and methods for capturing crowd wisdom in developing individualized treatment plans. More particularly, the invention is related to a system for data mining crowd sourced structured health related information and unstructured medical narratives and storytelling to identify treatment plans and general techniques that individuals with chronic diseases/symptoms can use to improve their general health and well being. The data mining can be from a wide variety of sources, including the internet, social media, clubs, websites and communities of subjects created for the data mining. The mining can be done using machine learning AI, including deep learning, to find potential treatments.

Embodiments of the invention include systems and methods for capturing crowd wisdom in developing individualized treatment plans. More particularly, the invention is related to a system for data mining crowd sourced structured health related information and unstructured medical narratives and storytelling to identify treatment plans and general techniques that individuals with chronic diseases/symptoms can use to improve their general health and wellbeing. The crowd wisdom is captured by an information management system that has a processing unit that stores a number of software agents. The software agents include a data extraction application that extracts, identifies and links associated processed data from the structured database, the unstructured database and the internet usage database.

Crowd wisdom on disease treatment can be captured from participants in an information management system. Preferably, the participants suffer the disease or condition being investigated for treatment, or are caregivers for the sufferers, with first hand knowledge of treatment effectiveness. The participants should be screened for obvious bias, such as a financial interest in particular treatments.

The crowd wisdom can be preferably collected from participants using a questionnaire, for example, by sending the questions to their mobile device (such as a smart phone or through a computer). The questions would focus on the specifics of the treatment regime and its application; e.g., the dosage and frequency (if the treatment is a drug, food or other consumable) or how to perform exercise routines and their duration (if they are the treatment). One can also perform data extraction and analysis, using an application to data mine the structured health related information such as medical records, pharmacy records, unstructured medical narratives such as storytelling, and internet usage data to identify treatment plans and general techniques that individuals with diseases/symptoms use. The subjects can also be individually monitored to try to determine the source of symptom relief, if they are unaware of why their symptoms might periodically improve.

The crowd wisdom from the foregoing sources is sent to a processing unit with a number of software agents and data extraction applications, including inference engines, that it uses to identify and associate relevant information in each data source and to correlate and link the relevant information identified in each data source to build a searchable combined information system, that is communicated to a web portal or platform. The combined information system on the web portal or platform is searchable and downloadable to a user through a mobile device controlled by, e.g., an application or software agent which instructs and configures communication between the combined information system and the mobile device.

In one embodiment of the information management system, the unstructured data will include a daily logging of users daily symptoms, general wellbeing, habits and routines. The collective wisdom of thousands of participants captured within these daily medical narratives and personal experiences will be processed using various algorithmic based data extraction applications. For example, common themes of symptoms, daily routines, and treatments plans (medically recommended and user determined alternative health treatments) will be extracted and correlated using a variety of software analytic engines such as natural language processing, inference engines, and by following Markov patterns. The key is to dissect these conversations and stories for patterns of commonality as well as unique patterns that offer insights into the best practices for achieving the best outcomes. The analytic engines will extract information from the medical narratives, match and compare the information extracted from participants and assess similarities and differences. The similarities and differences will be collated and analyzed to extract common information, on what are widely agreed to be effective treatments by participants. The more widely effective treatments would be first preference for clinical trials or participant testing.

The invention also includes rigorous testing of proposed treatments by first determining a set of IBD indicators which can be objectively measured, and then performing the indicator measurements in subjects reporting symptom relief from a treatment to determine if the indicators correlate with the expected pattern for symptom relief. The objective indicators include measurement of hydrogen and/or methane off gassing of an IBD subject's breath (or from feces). Embodiments of the invention are related to a system providing a hydrogen and/or methane sensor device and a wireless platform in communication with the sensor device to periodically analyze the hydrogen and/or methane off gassing of an IBD subject's breath (or from feces) and correlating the levels of hydrogen and/or methane with symptoms or Events. For preferably determining levels of hydrogen and/or methane, subjects periodically measure methane and hydrogen in the breath, using a wireless device which sends the results to a server. See e.g., US Publ'n No. 20180271404 (disclosing a methane and hydrogen sensor for breath, to integrate with a smartphone or other device). Subjects report their symptoms and food intake, preferably using a wireless device which sends the results to the server. One preferred method for measuring the hydrogen/methane in a fecal sample, is to include a tube running from upper chamber 104 and detachably connecting to the breath sampler device (as described in U.S. Publ'n No. 20180271404), which then measures the levels of hydrogen/methane in the fecal sample from the gas level in chamber 104.

Referring to FIG. 1, it shows a fecal sampling kit 100 with a spatula 50 and a fecal sample container 101. Spatula 50 can be used by the subject to scoop a small measured amount of fecal matter into chamber 106. As noted in the Summary, hydrogen and/or methane is preferentially measured from the subject's breath, using a device as described in US Publ'n No. 20180271404. But it could also be measured from a fecal sample, where a relatively standard volume of fecal material 52 is placed in chamber 106, and the off gassed hydrogen or methane is measured. When measured from the fecal sample, the same device for measuring hydrogen and/or methane from the subject's breath can be attached (using a tube, for example) to a port in the upper chamber 104 of fecal sample container 101.

Referring to FIGS. 3A to 4C, fecal sample container 101 has a threaded cap 102 with two chambers, 104, 106, each of which is sealed but can be accessed by spatula, 50, carrying a solid, like fecal sample 52. Upper chamber 104 is sealed from the environment and capable of collecting gases from a sample 52 in the cap's lower chamber 106. The lower trap door of the lower chamber 106 is opened by e.g., twisting the cap 102 to allow sample 52 therein to fall into container 101.

An automatic timer 225 in cap 102 is activated by a sensor, which detects when the port on the side of chamber 106 is opened for the sample to enter. The automatic timer 225 is preferably set to limit the gas measurement by a gas sensor (now shown) for a specific period of time (e.g., 10 seconds, 20 seconds). Several off gassed hydrogen/methane measurements are taken in succession and stored as individual values specific for a particular fecal sample of the individual subject. All measurement values and related subject information for a specific fecal sample are recorded and then transferred to a data processor, preferably wirelessly, such as by Bluetooth to a mobile phone or other wireless device.

After cap 102 is manipulated to open the lower chamber 106, the lower trap door in chamber 106 opens and fecal sample 52 falls into container 101. Cap 102 is twisted again to seal sample 52 in container 101. Container 101 is then shipped for fecal sample analysis and/or optionally methane and hydrogen gas analysis, or, optionally VOC analysis of the gas collected in the upper chamber 104. Optionally the fecal sampling kit 100 may also contain a sealable impermeable pre-addressed bag that the fecal sample container 101 is placed into for mailing to a laboratory for analysis. The fecal sample 52 analysis can be for levels of the compounds in Tables A and B above, genetic markers associated with IBD, levels of gene expression correlating with IBD, and the bacterial composition of the sample.

Figure 7A:
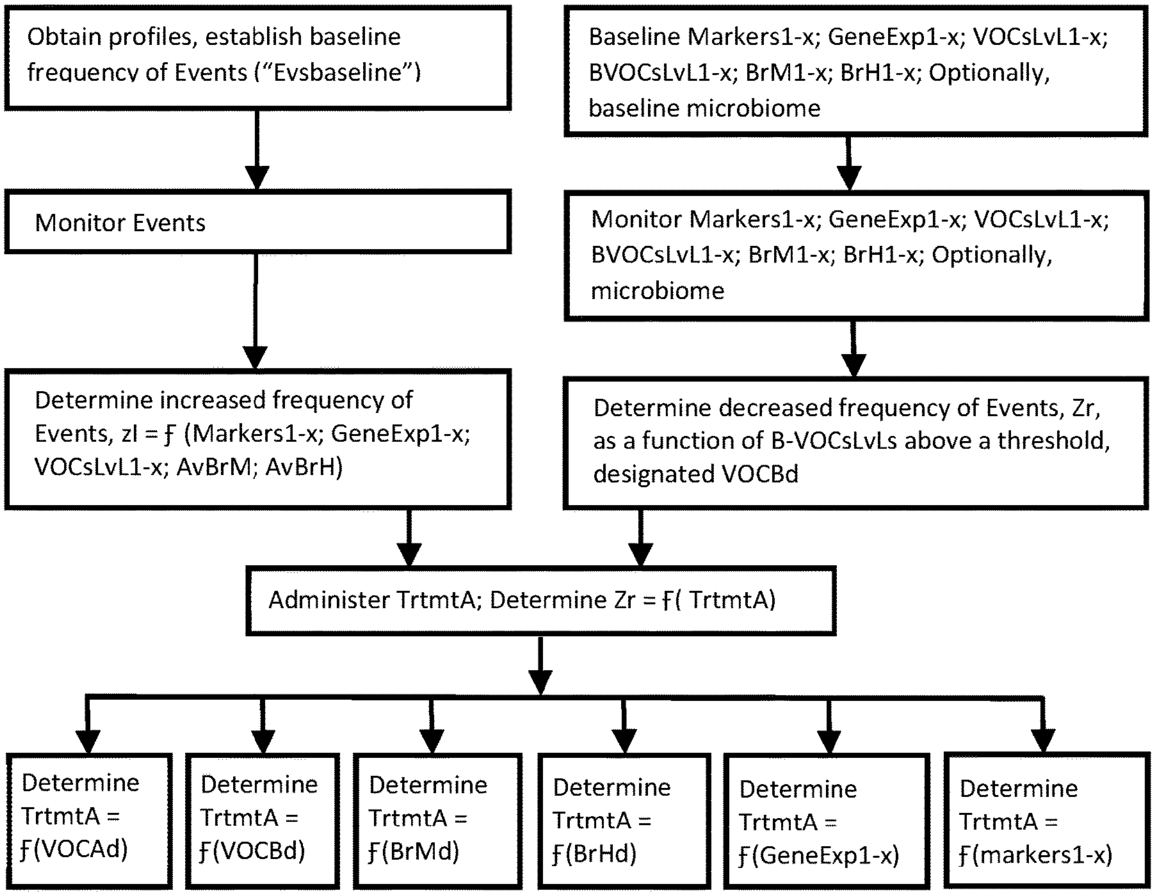
FIGS. 7A and 7B are two successive pages of a flow chart showing a method for determining correlations between (independent variables) certain genetic markers, gene expression levels, volatile organic compound levels, and hydrogen and methane levels in the breath (or feces), to both adverse events and to practicing an unregulated therapy, for IBD patients. It further shows how to confirm the correlation for an individual with IBD, and messaging that individual to adhere to a demonstrably efficacious therapy; and optionally, messaging the individual to adhere to the therapy more strictly (if the data and analysis indicates the therapy should be effective).
Figure 7B:
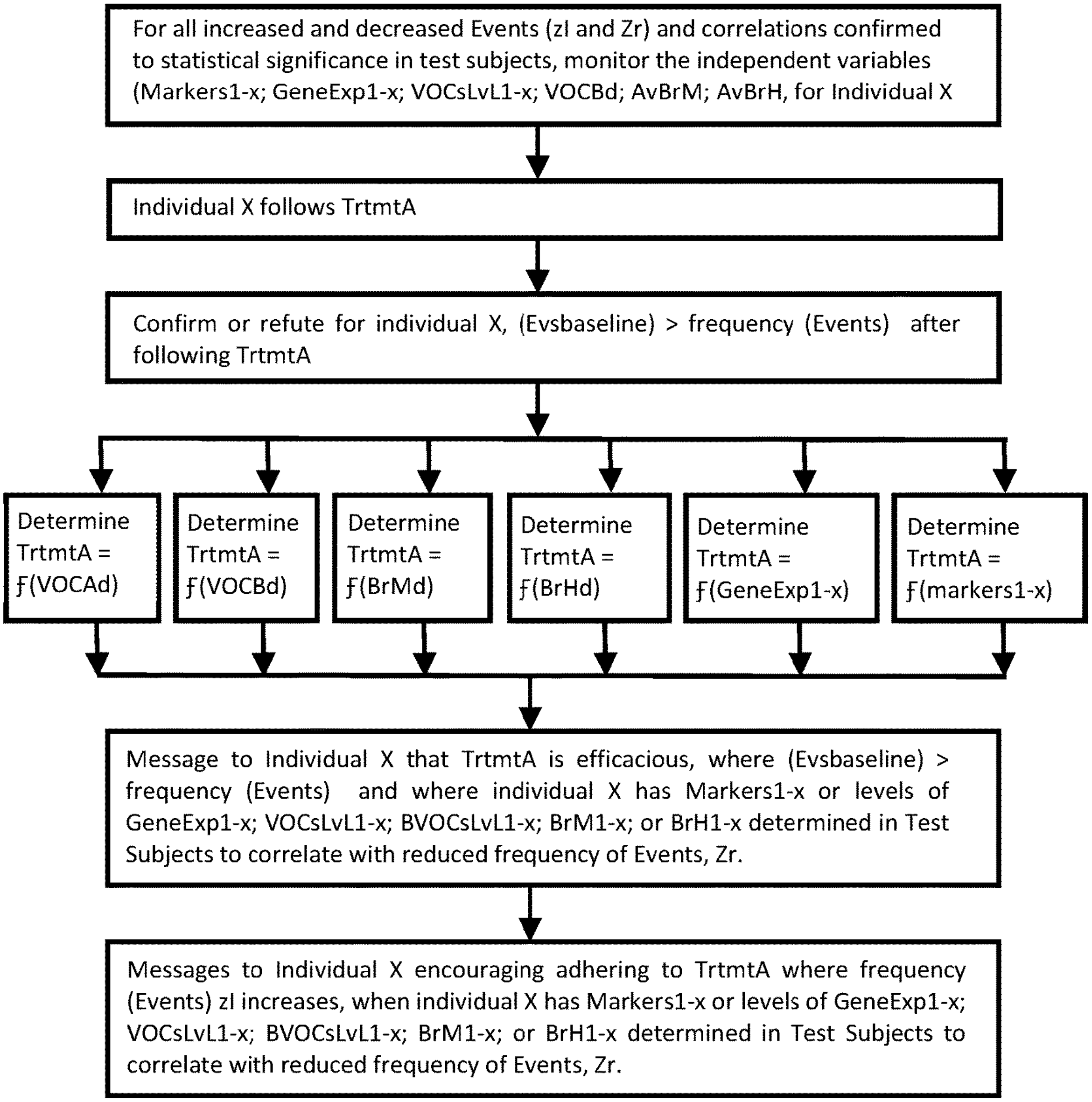

Following finding of potential treatments through crowd-sourcing, public documents or other methods, these treatments are tested in a group of test subjects. FIGS. 7A, 7B outline the testing and verification of effective treatments in a group of test subjects for sufferers which exhibit symptoms as Events; for example, for those with inflammatory bowel disease (IBD), Events would include frequent diarrhea, high frequency flatulence, and high frequency bowel movements. The baseline frequency of Events ("Evsbaseline") is established for each test subject before starting treatment. In FIGS. 7A, 7B, where the steps are shown in flow chart form with limited explanation, the following steps 1 to 22 are a comprehensive explanation of the steps in the FIGS. 7A, 7B process. Events can be determined directly from subject's reporting, or from external sources such as medical, medical insurance or pharmacy records or reports.

1) Obtain details of health of each test subject: health profiles, and past and present ailments to establish the baseline frequency of Events ("Evsbaseline") and prepare test subjects on how to report ("Events" or "symptoms");
2) Where IBD treatments are being tested: perform baseline fecal sample collection for test subjects to initially determine: (i) DNA and/or RNA markers for wild type and mutant beneficial or detrimental bacterial strains in the gut microbiome ("Markers1-x"); (ii) gene expression of any candidate genes (from the individual or the microbiome bacteria) whose expression is elevated or decreased in the test subjects from normal ("GeneExp1-x"); (iii) levels of volatile organic compounds in Table A above ("VOCsLvL1-x") and in Table B above ("B-VOCsLvL1-x") associated with test subjects, where the VOCsLvL and B-VOCsLvL can be measured from gas associated with the fecal sample; and (iv) determine from a breath sensor carried by test subjects the methane ("BrM1-x") and hydrogen levels ("BrH1-x") in each subjects' breath (or feces), where 1-x indicates a reading at a different time for methane and hydrogen levels, which can be transmitted to a server;
3) Monitor treatment of each test subject using a wireless device which allows input of all information about the treatment (TrtmtA);
4) Monitor each test subject's frequency of Events using the wireless device, which allows their entry and category;
5) Collect fecal samples at intervals for each test subject: and monitor changes in Markers1-x; GeneExp1-x; VOCsLvL1-x; and B-VOCsLvL1-x; Optionally: BrM1-x or BrH1-x, preferably, determine the average of the readings ("AvBrM" and "AvBrH") during each collection period; (Optionally, monitor the methane ("M1-x") and hydrogen levels ("H1-x") in each subjects' fecal sample and use those measures for AvBrM and AvBrH, instead of measuring them from the subject's breath.)
6) Use a software agent to determine dependency of increased frequency of Events, zI (as the dependent variable), with the independent variables being: Markers1-x; GeneExp1-x; VOCsLvL1-x; AvBrM; AvBrH; wherein all independent variables are determined across all test subjects; using a software agent which (i) determines correlation of zI with each independent variable using a univariate hypothesis test, where the null hypothesis is "the presence of this marker, or this level of gene expression or greater, or this level of volatile organic compounds or greater, or these levels of hydrogen and methane or greater, are not associated with zI"; where such markers are designated Md, such gene expression levels are designated GEd, such levels of organic compounds are designated VOCAd; such average levels of methane are designated; BrMd, and such average levels of hydrogen are designated BrHd (ii) performs a multivariate regression model of all possible combinations of the independent variables Markers1-x; GeneExp1-x; and VOCsLvL1-x, AvBrM; AvBrH with substantially the same null hypothesis as in step (i) but where the word "or" is "and"; to represent the combination of independent variables modeled, where the following formula represents this multivariate regression model:

$$zI = f(\text{Markers1-}x;\text{GeneExp1-}x;\text{VOCsLvL1-}x;\text{AvBrM};\text{AvBrH})$$

Determine the independent variables and combinations thereof where the dependency of increased frequency of Events, zI, is established at a confidence interval (CI) of at least 95% for the appropriate null hypothesis noted above in steps (i) and (ii); for markers Md, for gene expression levels GEd, for levels of organic compounds VOCAd; for levels of methane AvBrM; and for levels of hydrogen AvBrH.

7) Use a software agent to determine dependency of increased frequency of Events, zI (as the dependent variable), with the dependent variable being TrtmtA, as represented by the formula:

$$zI = f(\text{TrtmtA})$$

where the dependency of increased frequency of Events, zI, is established at a confidence interval (CI) of at least 95% (where the null hypothesis is: "failure to follow TrtmtA is not associated with increased frequency of Events, z";

8) Use a software agent to determine dependency of decreased frequency of Events (as the dependent variable, Zr), with the independent variable being a level of volatile organic compounds in Table B ("B-VOCsLvL1-x") above a threshold associated with normal subjects or remission (see specification), where the B-VOCsLvL can be measured from gas associated with the fecal sample, and where such dependency is established at a confidence interval (CI) of at least 95% (where the null hypothesis is: "Levels of B-VOCsLvLs above this threshold are not associated with decreased frequency of Events, Zr"; where such levels are designated VOCBd), where the following formula represents this step 8:

$$Zr = f(\text{BVOCsLvL1-}x)$$

9) Use a software agent to determine correlation between TrtmtA and levels of VOCBd (above the threshold):

$$\text{TrtmtA} = f(\text{VOCBd})$$

at a confidence interval (CI) of at least 95%, by using as a null hypothesis: "TrtmtA does not correlate with levels of VOCBd above the threshold."

10) Use a software agent to determine correlation between TrtmtA and levels of VOCAd (below the threshold):

$$\text{TrtmtA} = f(\text{VOCAd})$$

at a confidence interval (CI) of at least 95%, by using as a null hypothesis: "TrtmtA does not correlate with levels of VOCAd below the threshold."

11) Use a software agent to determine correlation between TrtmtA and levels of methane BrMd (below the threshold):

$$TrtmtA=f(BrMd)$$

at a confidence interval (CI) of at least 95%, by using as a null hypothesis: "TrtmtA does not correlate with levels of BrMd below the threshold."

12) Use a software agent to determine correlation between TrtmtA and levels of hydrogen BrHd (below the threshold):

$$TrtmtA=f(BrHd)$$

at a confidence interval (CI) of at least 95%, by using as a null hypothesis: "TrtmtA does not correlate with levels of BrHd below the threshold."

13) Based on an individual X's profile determine if TrtmtA is appropriate for individual X to minimize Events; and provide the steps and procedures for TrtmtA to individual X on the wireless device;

14) Monitor individual X's compliance with TrtmtA and frequency of Events, based on entries in individual X's wireless device;

15) Confirm or refute for individual X correlation of TrtmtA with decreased frequency of Events ("Zr") as compared with Evsbaseline; i.e., individual X following TrtmtA results in (Evsbaseline)>frequency (Events);

16) Confirm or refute for individual X, a decreased frequency of Events (Zr) as compared with Evsbaseline; for each of: gene expression levels<GEd, VOCsLvL<VOCAd, and B-VOCsLvL>VOCBd; AvBrM<BrMd; AvBrH<BrHd; and an increased frequency of Events (zI) as compared with Evsbaseline (i.e., frequency (Events)>(Evsbaseline)) with the presence of markers Md in the sample;

17) Confirm or refute for individual X that TrtmtA correlates with levels of VOCAd (below the threshold) (Correlation A);

18) Confirm or refute for individual X that TrtmtA correlates with levels of VOCBd (above the threshold) (Correlation B);

19) Confirm or refute for individual X that TrtmtA correlates with levels of BrMd (below the threshold) (Correlation C);

20) Confirm or refute for individual X that TrtmtA correlates with levels of BrHd (below the threshold) (Correlation D);

21) If individual X shows a decreased frequency of Events (Zr) where any of the following are true: VOCsLvL<VOCAd; B-VOCsLvL>VOCBd; AvBrM<BrMd; AvBrH<BrHd; and markers Md are absent; and if any of Correlations A through D are established for individual X, but individual X does not show decreased frequency of Events by following TrtmtA, message individual X to carefully monitor compliance with TrtmtA; and 22) If individual X shows decreased frequency of Events when following TrtmtA, and shows increased frequency of Events when not following TrtmtA: message individual X about (i) TrtmtA and/or the importance of consistently following TrtmtA and (ii) specifying in the messages steps to take to conform to TrtmtA.

The steps 1-22 above and FIGS. 7A, 7B provides a rigorous analysis of a number of data points from test subjects, with the objective to provide an effective treatment for an individual. It shows further, how to construct messages for the individual to adhere to or optimize the diet to reduce symptoms of IBD. FIGS. 6A, 6B summarize steps 1-22 in equation form.

Figure 5A:
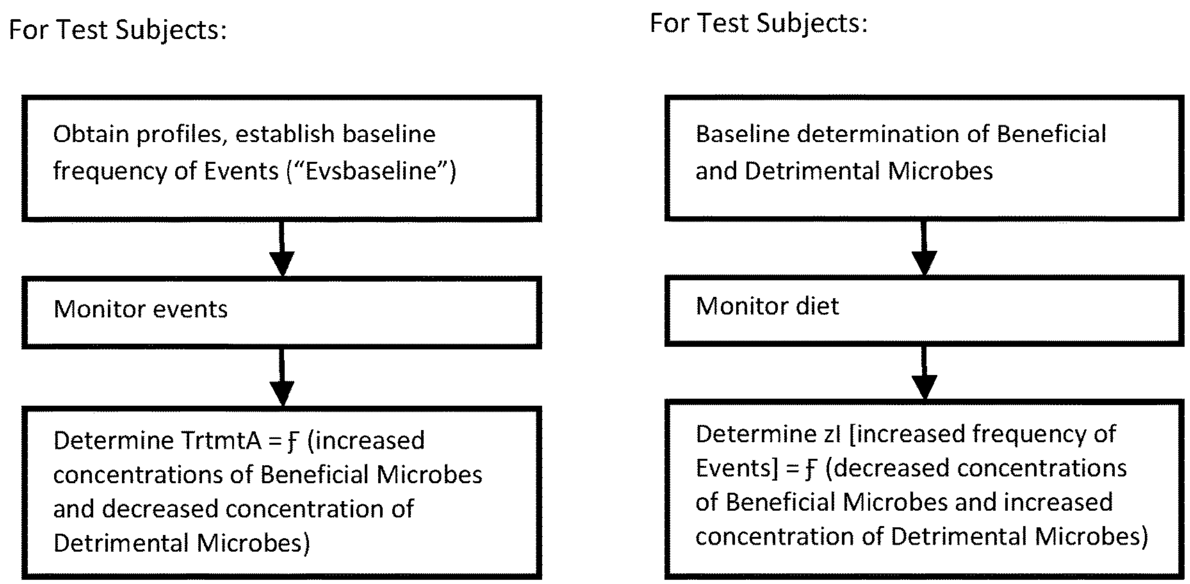
FIGS. 5A and 5B are two successive pages of a flow chart showing a method for determining correlations between (independent variables) certain genetic markers, gene expression levels, volatile organic compound levels, and hydrogen and methane levels in the breath, to both adverse events and particular treatments, for IBD patients. It further shows how to confirm the correlation for an individual with IBD, and messaging that individual.
Figure 5B:
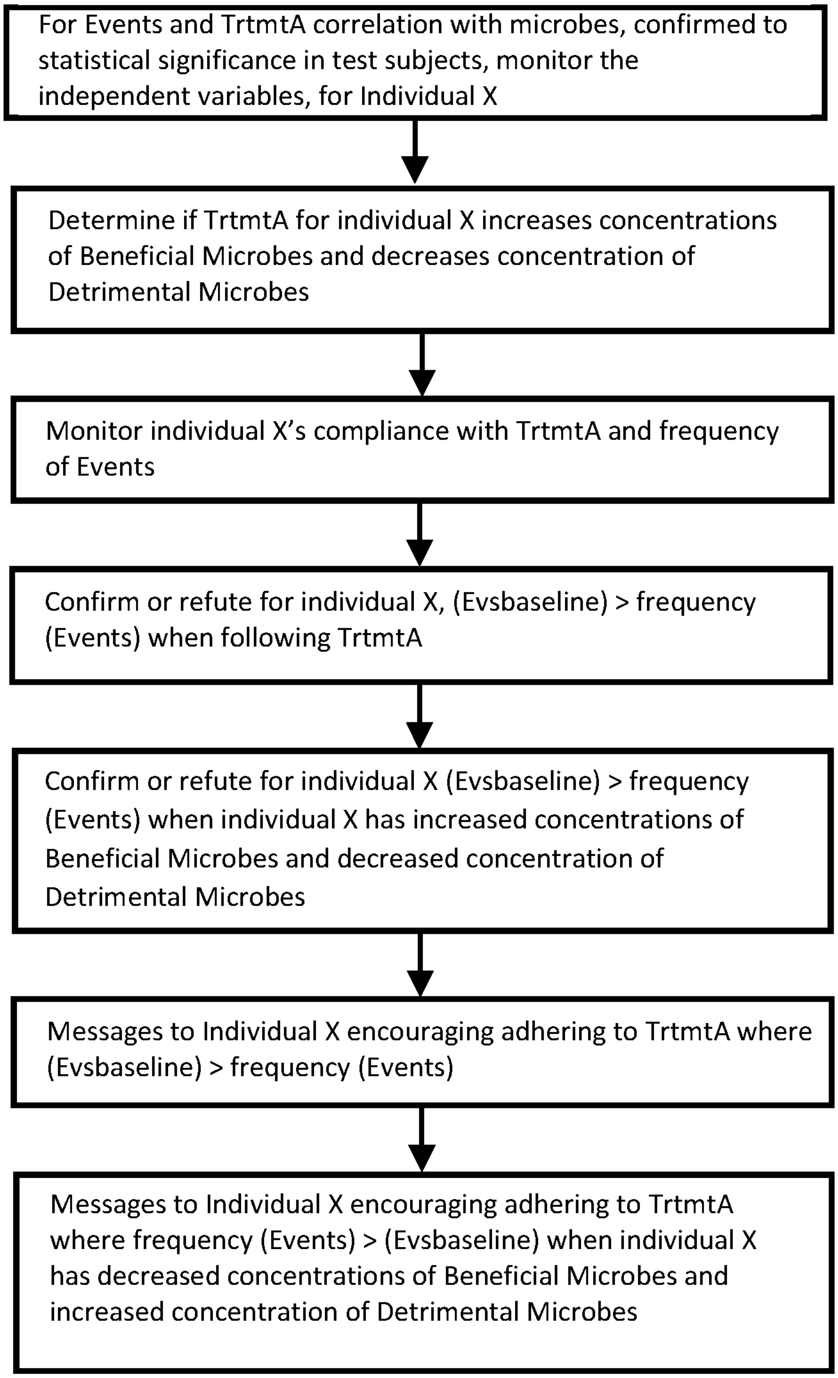

Another set of data points can also be analyzed and then applied to an individual, in addition to those in FIGS. 7A, 7B and steps 1-22 above. For the steps in FIGS. 5A, 5B (and the steps 1a et seq below) it is assumed that the correlation in step 7 above, i.e., $zI=f(TrtmtA)$, had previously been established in test subjects.

These data points relate to the composition of the gut's bacteria, also known as the microbiome.

1a) Obtain details of digestive health of each test subject: health profiles, and past and present digestive ailments i.e.: whether suffering from IBS, IBD, frequent diarrhea, high frequency flatulence, high frequency bowel movements ("Events" or "symptoms"), and also the baseline frequency of Events, ("Evsbaseline");

2a) Perform baseline fecal sample collection for test subjects to initially determine: (i) concentrations of Bifidobacteria, *Lactobacillus, Faecalibacterium prausnitzii* and Propionibacteriaceae ("Beneficial Microbes"); (ii) concentrations of *Bacteroides fragilis*, Ruminococcaceae and *Clostridium* ("Detrimental Microbes"); (iii) presence of any mutants of Beneficial Microbes or Detrimental Microbes (based on presence of any Markers1-x) which are associated with Zr (referred to as Mutants).

3a) Monitor compliance of each test subject using a wireless device which allows input of steps relating to TrtmtA; with recommendations on screen for how to do so;

4a) Collect fecal samples at intervals for each test subject and monitor concentrations of Beneficial Microbes, Detrimental Microbes and Mutants, during each collection period;

5a) Use a software agent to determine correlation of TrtmtA with decreased concentrations of Beneficial Microbes, increased concentration of Detrimental Microbes and absence of Mutants; and using a univariate hypothesis test, where the null hypothesis is "TrtmtA is not associated with increased concentrations of Beneficial Microbes, decreased concentration of Detrimental Microbes and absence of Mutants" at a confidence interval (CI) of at least 95% for the null hypothesis;

6a) Use a software agent to determine correlation of increased frequency of events, zI, with decreased concentrations of Beneficial Microbes, increased concentration of Detrimental Microbes and/or presence of Mutants.

7a) If the correlation in step 5a or 6a is established at a confidence interval (CI) of at least 95% for the null hypothesis, confirm or refute for individual X the correlation between TrtmtA and/or zI with decreased concentrations of Beneficial Microbes, increased concentration of Detrimental Microbes and presence of Mutants;

8a) if the correlation in step 5a is established for individual X, but individual X reports compliance with TrtmtA and fecal samples do not show increased concentrations of Beneficial Microbes, decreased concentration of Detrimental Microbes and absence of Mutants; send messages to individual X to accurately report steps taken in TrtmtA, or identify why the failure to increase concentrations of Beneficial Microbes and decrease concentration of Detrimental Microbes and reduce Mutants occurred; and 9a) If individual X shows increased concentrations of Beneficial Microbes, decreased concentration of Detrimental Microbes and absence of Mutants when following TrtmtA, and shows the opposite when not following TrtmtA: message individual X about (i) the importance of consistently following TrtmtA and (ii) specifying in the messages how to conform individual X's activities to TrtmtA based on the information reported by individual X.

FIGS. 6A, 6B outline another related embodiment, in equation form, where a genetic marker or gene expression level is determined to predispose test subjects to IBD or Events in test subjects, after going through the steps 1 to 12 above; one can go through steps 13 to 22 above for an individual Y with the marker or gene expression level, and determine if increased frequency of Events is dependent on TrtmtA. The same treatment in steps 21 and 22 can be used, if so. If not, one can modify TrtmtA for an individual (individual Y), and if determined to be effective in ameliorating IBD or reducing frequency of Events, perform similar monitoring of individual Y's adherence to the treatment regimen, by monitoring the same indicators as in steps 13 to 20 and/or 5a and 6a. Again, where these indicators indicate individual Y is not adhering to the treatment regime, messages can be sent instructing adherence, and the importance of doing so. Again, the various indicators (like VOCsLvL1-x; B-VOCsLvL1-x; AvBrM; AvBrH) can also serve as a verification of individual Y's adherence to the treatment regime, and whether individual Y is truthfully reporting compliance with the treatment regime. Messages can be sent about the importance of compliance with the treatment regime when the indicators predict an increase in frequency of Events; whether or not such increase is reported by individual Y. Another related embodiment is to standardize messaging to test subjects and individuals. The first step in message selection, for querying the subject's condition and for instructing treatment, is establishing, initially, a testing a set of messages for each domain, and verifying that the messages are not confusing or ambiguous or difficult to understand and correctly answer. This is accomplished by determining Cronbach's Alphas for a set of messages sent to users. For a quantity which is a sum of $K$ components (also called testlets or items) X=Y1+Y2+Y3 . . . YK, Cronbach's alpha is defined as:

$$\alpha = \left(\frac{k}{k-1}\right)\left(1 - \frac{\sum_{i=1}^{k}\sigma^2_{y_i}}{\sigma^2_x}\right)$$

where $\sigma^2x$ is the variance of the observed total scores from subjects/individuals and where $\sigma^2_{Yi}$ is the variant of component i for the responding subjects/individuals.

To apply Cronbach's alpha in formulating a database of clear questions, for each test subject and user, one compares the sum of items' variance (through the whole set of responses from test subjects and users) to the variance of the sum of the total test scores. If the sum of items' variance is significantly greater than the variance of the sum of the total test scores, it means that the portion of the errors resulting from misinterpretation, confusion, misunderstanding or related reasons is large, and the status the questions are designed to determine is unreliable. In such cases, the questions need to be reformulated and the new questions need to be tested for reliability using Cronbach's alpha again. The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A fecal sample gas detecting system comprising:

a fecal container comprising a first sealed chamber, wherein the first sealed chamber comprises a twistable cap and a fecal port for admitting a fecal sample into the first sealed chamber;

the container further comprising a gas sensor connected to the first sealed chamber wherein the gas sensor is capable of detecting and measuring methane gas levels and hydrogen gas levels released into the first chamber from an admitted fecal sample;

the container further comprising a second sealed chamber configured to admit a fecal sample after measurement of methane gas and hydrogen gas;

wherein the first and second sealed chambers are connected by a trap door, the trap door controlled by twisting the cap to cause the fecal sample to fall into the second sealed chamber; and wherein the container further comprises a timer for automatically setting a time period during which methane gas and hydrogen gas levels are measured by the gas sensor.

2. The method container of claim 1 wherein the cap of said container is configured to twist to open or close the trap door.

3. The container of claim 1 wherein the timer is activated by a sensor which detects when the fecal port is opened.

4. The container of claim 1 wherein the first sealed camber comprises the port, sensor, cap, timer, and trap door and is detachable from the second chamber, thereby unsealing the second sealed chamber.

5. The container of claim 1 wherein the fecal port comprises a port control in operable connection with the cap for opening and closing the fecal port.

6. The system of claim 1 wherein the container comprises a tube connected to the first chamber and sensor.

7. The system of claim 1 comprising a spatula configured to fit into the fecal port.

8. The system of claim 1 comprising a wireless device in communication with the sensor.

9. The system of claim 8 wherein the wireless device is configured to be in communication with a server.

* * * * *